United States Patent [19]

Parron

[11] Patent Number: 4,814,499
[45] Date of Patent: Mar. 21, 1989

[54] PROCESS FOR PREPARATION OF SUBSTITUTED PHENYLUREAS

[75] Inventor: Jean C. Parron, Caluire, France

[73] Assignee: Rhone-Poulenc Agrochimie, Lyons, France

[21] Appl. No.: 827,782

[22] Filed: Feb. 7, 1986

[30] Foreign Application Priority Data

Nov. 2, 1985 [FR] France ................. 85 02079

[51] Int. Cl.$^4$ ........................... C07C 127/19
[52] U.S. Cl. ...................... 564/52; 564/48; 564/53; 564/54
[58] Field of Search .............. 564/48, 52, 53, 54

[56] References Cited

U.S. PATENT DOCUMENTS

| | | | |
|---|---|---|---|
| 2,673,877 | 10/1951 | Thompson | 564/53 |
| 2,729,677 | 1/1956 | Gilbert et al. | 564/53 |
| 2,768,971 | 10/1956 | Jones | 564/53 |
| 2,878,284 | 3/1959 | K'Burg | 564/53 |
| 3,177,249 | 4/1965 | Martin et al. | 564/54 X |

FOREIGN PATENT DOCUMENTS

DE-B-
1064051  8/1959  Fed. Rep. of Germany ........ 564/48

Primary Examiner—Charles F. Warren
Assistant Examiner—Carolyn S. Greason
Attorney, Agent, or Firm—Morgan & Finnegan

[57] ABSTRACT

Process for preparing a substituted phenylurea.

A suitably substituted aniline, excess urea in a mole ratio of at least 1.1 with respect to the aniline, and a secondary amine are reacted simultaneously in a non-hydroxyl-containing organic solvent at a temperature of 130° to 250° C., with removal of ammonia as it forms.

The phenylureas obtained are used as herbicides.

28 Claims, No Drawings

PROCESS FOR PREPARATION OF SUBSTITUTED PHENYLUREAS

The present invention relates to a new process for preparing a trisubstituted N-phenylurea, as well as the products obtained by this process.

Some N-phenylureas substituted on the benzene ring are known in respect of their use as herbicides, either total herbicides or herbicides which are selective on certain crops. There may be mentioned, in particular, N-(4-chlorophenyl)-N',N'-dimethylurea(monuron), N-(3,4-dichlorophenyl)-N',N'-dimethylurea(diuron), N-(4-isopropylphenyl)-N',N'-dimethylurea(isoproturon), N-(3,4-dichlorophenyl)-N'-methyl-N'-n-butylurea(neburon), N-(3-chloro-4-methylphenyl)-N',N'-dimethylurea(chlortoluron), N-(3-chloro-4-methoxyphenyl)-N',N'-dimethylurea (metoxuron), N-(3-trifluoromethylphenyl)-N',N'-dimethylurea (fluometuron) and N-(3,4-dichlorophenyl)-N'-methyl-N'-methoxyurea (linuron).

On account of the large quantities in which they are used, these compounds need to be manufactured by industrial processes. The most extensively used process consists in reacting the suitably substituted phenylisocyanate with the appropriate N,N-disubstituted amine. This process gives results (yield, purity of the products) which are generally acceptable. However, the production sequence involves the manufacture of the relevant phenylisocyanate, which is most frequently accomplished by the action of phosgene on the corresponding aniline. This reaction demands an installation which requires many safety measures, and much corresponding investment, on account of the attacking properties and toxicity of phosgene. Moreover, even under these conditions, the risk of leakage is not zero, and always constitutes a threat at the site of manufacture and to the environment.

To avoid this disadvantage, it has been proposed to manufacture N-phenyl-N',N'-dimethylureas, monuron and diuron, by the action of the corresponding aniline on urea in the presence of alcohol or phenol, and then, in a second stage, by reacting gaseous dimethylamine, with removal of the ammonia formed.

Another method proposed consists in reacting the three reagents together, but this requires the use of a fourth reagent, asymmetric dimethylurea, and the reaction to be performed in a molten medium, thereby leading to yields of the order of 70%, which are consequently insufficient for economically profitable working.

To deal with the growing demand for certain herbicides belonging to this family, the need consequently exists to find a process which possesses the dual advantage of providing a product in excellent yield and in high purity, and of not posing a threat to either the manufacturing personnel or the environment.

Now, the Applicant Company has specifically discovered that it was possible to achieve this dual object by means of a new process not involving the use of phosgene.

More specifically, the present invention relates to a process for preparing a trisubstituted N-phenylurea, wherein the corresponding aniline, urea in a mole ratio with respect to the aniline of at least 1.1, and the corresponding secondary amine are reacted simultaneously in a non-hydroxyl-containing solvent medium at a temperature of between 130° and 250° C., with removal of ammonia as it is formed, according to the scheme:

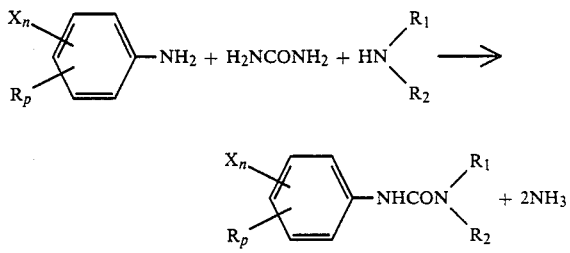

in which:
X is a halogen atom, preferably chlorine or bromine, at position 3 and/or 4,
n is an integer equal to 0, 1 or 2,
R is an alkyl radical having 1 to 4 carbon atoms, or an alkoxy group having 1 to 4 carbon atoms, and optionally halogenated, or an alkoxy group having 1 to 4 carbon atoms, at position 3 or 4 on the benzene ring,
is an integer equal to 0 or 1, preferably with the further provision that n+p is equal to 2 at most,
$R_1$ and $R_2$, which may be identical or different, are each an alkyl radical having 1 to 4 carbon atoms, or alternatively one of them is an alkyl radical having 1 to 4 carbon atoms and the other is an alkoxy radical having 1 to 4 carbon atoms.

The starting aniline is preferably chosen from the group consisting of p-chloroaniline, 3,4-dichloroaniline, 3-chloro-4-methylaniline, para-cumidine, 3-chloro-4-methoxyaniline and 3-trifluoromethylaniline.

Urea is used in excess so that the mole ratio with respect to the starting aniline is at least 1.1, and preferably 1.25 to 2.

In the formula of the N,N-dialkylamine, at least one of the radicals $R_1$ and $R_2$ is advantageously a methyl group. $R_1$ and $R_2$ are both preferably a methyl radical.

The reaction is performed in a solvent medium consisting of an inert organic solvent not containing a hydroxyl radical in its formula. Polar or non-polar solvents are used, e.g. amides such as dimethylformamide or dimethylacetamide, ketones, e.g. cyclohexanone, aliphatic hydrocarbons, optionally chlorinated, or aromatic hydrocarbons, optionally chlorinated, such as toluene or chlorobenzenes, especially monochlorobenzene, ortho-dichlorobenzene and 1,3,5-trichlorobenzene.

The concentration of the reagents in the solvent can vary over a wide range of proportions, e.g. from 5 to 80%. This depends on the solubility, and consequently on the nature of the reagents and that of the solvent. It has been observed that good results are obtained for concentrations from 15 to 60%.

The reaction is performed by heating to a temperature of between 130° and 250° C., and preferably between 160° and 225° C. Lower temperatures give rise to an insufficient reaction rate, while at excessively high temperatures conditions are difficult to control at the industrial level and less profitable.

The process according to the invention is performed under good conditions at atmospheric pressure. However, an overpressure resulting from partial pressure of dialkylamine or from an overpressure generated internally through a rise in the reaction temperature, can enable the reaction time to be reduced. This overpressure can generally be up to 10 atmospheres.

Under the conditions described above, the ammonia is removed as it forms.

Successive operations are possible, using the mother liquors from one operation for a succeeding operation.

EXAMPLE 1

In a 500-cc four-necked flask equipped with a stirrer and condenser, distilled para-cumidine (54 g; 0.4 mole), urea (36 g; 0.6 mole), equivalent to a 50% excess with respect to the stoichiometry, and orthodichlorobenzene (200 g) are charged. The mixture is brought to boiling (180° C.) and dimethylamine at 60° C. is introduced by bubbling. The mixture is left to react for approximately 6 hours, and the temperature rises to 85° C. The ammonia produced is removed as it forms. The heating is then stopped and the mixture left to cool to 100° C. The admission of dimethylamine is then stopped (total amount introduced 195 g) and the mixture is cooled in a water bath at 20° C. A precipitate is obtained which is filtered off, drained and washed twice with ortho-dichlorobenzene. The precipitate is taken up in cold water and the solvent separated and recovered by entrainment, with stirring, at 100° C. The solution is then cooled to 20° C. and filtered, and the product washed with water and dried in the oven. A dry product (61 g) is obtained containing N-(p-isopropylphenyl)-N',N'-dimethylurea (59.2 g; 97% purity) and dicumylbiuret (0.43 g).

EXAMPLE 2

The procedure is as in Example 1, except that the reaction is performed so that the theoretical final concentration of phenylurea is 15% by weight, and for 4 hours at 180° C., and that the excess amount of urea is varied. The yields and the purity of the product obtained after a single operation are recorded in Table 1 below:

TABLE 1

| Excess urea as mole ratio | 1 | 1.10 | 1.25 | 1.50 | 2.0 |
|---|---|---|---|---|---|
| True yield % | 55 | 57 | 72 | 73 | 69 |
| % purity of IPU | 70 | 93 | 94 | 98 | 99 |

The table above shows clearly that the stoichiometric conditions are not satisfactory from the standpoint of either the yield or the purity of the product obtained, and that sufficient excess urea is required for conditions to be obtained which are acceptable at the industrial level.

EXAMPLE 3

The procedure is as in Example 1, except that the reaction is performed so that the theoretical final concentration of N-(4-isopropylphenyl)urea is 45% by weight, and for 10 hours at 185°–188° C., and that the excess amount of urea is varied. The yields and the purity of the product obtained in a single operation are recorded in Table 2 below:

TABLE 2

| Excess urea as mole ratio | 1 | 1.10 | 1.20 | 1.30 | 1.40 |
|---|---|---|---|---|---|
| True yield % | 60 | 54.5 | 57 | 68.4 | 55.5 |
| % purity of iso-proturon | 93 | 96.5 | 97 | 98 | 98.5 |

EXAMPLE 4

The procedure is as in Example 1, ortho-dichlorobenzene being replaced as solvent by, respectively, cyclohexane and dimethylformamide. Similar results are obtained as regards both yield and purity of the isoproturon produced.

EXAMPLE 5

The procedure is as in Example 1, at 180° C. in ortho-dichlorobenzene and 205° C. in 1,3,5-trichlorobenzene, starting with cumidine (27 g; 0.2 mole) and urea (18 g; 0.3 mole) with a concentration of reagent of 15% in the reaction medium. Under these conditions, it is observed that at 205° and 180° C. the yield is quantitative after, respectively, 5 and 7 hours.

EXAMPLE 6

The procedure is as in Example 1, para-cumidine being replaced by, respectively, an equimolar amount of 3,4-rdichloroaniline, 3-chloro-4-methylaniline, 3-chloro-methoxyaniline, 3-trifluoromethylaniline and, in one case, dimethylamine being replaced by N-methyl-N-butylamine.

Under these conditions, the following are obtained, respectively:
N-(3,4-dichlorophenyl)-N',N'-dimethylurea
N-(3,4-dichlorophenyl)-N'-methyl-N'-n-butylurea
N-(3-chloro-4-methylphenyl)-N',N'-dimethylurea
N-(3-chloro-4-methoxyphenyl)-N',N'-dimethylurea
N-(3-trifluoromethylphenyl)-N',N'-dimethylurea.

Table 3 below gives, for each example, the starting substituted aniline and dialkylamine, the reaction time and also the true yield (TY) of corresponding substituted phenylurea and the purity thereof.

The structure of the phenylureas obhtained was confirmed by liquid phase chromatography and infrared and NMR spectrometry.

TABLE 3

| Substitution of the aniline | Dialkyl-amine | Reaction time | T Y % | % purity of the phenylurea | Melting point |
|---|---|---|---|---|---|
| 3,4-dichloro- | Dimethyl-amine | 6 h 30 min | 82 | 99 | 156° C. |
|  | Methyl-butylamine | 11 h | 72* | 98 | 100° C. |
| 3-chloro-4-methyl- | Dimethyl-amine | 6 h | 71 | 97.5 | 147° C. |
| 3-chloro-4-methoxy- | Dimethyl-amine | 7 h | 68 | 90 | 127° C. |
| 3-trifluoro-methyl | Dimethyl-amine | 13 h | 76 | 98 | 163–164° C. |

*The product is precipitated by removal of ortho-dichlorobenzene and by being taken up with hexane. This table shows clearly that the process according to the invention is applicable for the manufacture, under industrial conditions, of the principal commercial herbicidal phenylureas.

We claim:
1. A process for preparing a substituted N-phenylurea, by reacting a substituted aniline (I), urea (II) and a secondary amine (III) according to the following scheme:

$$X_n\text{-}\underset{R_p}{\underset{|}{\bigcirc}}\text{-}NH_2 + H_2NCONH_2 + HN\begin{matrix}R_1\\R_2\end{matrix} \longrightarrow$$

(I)　　(II)　　(III)

-continued

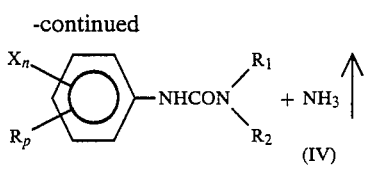

wherein
X is halogen meta and/or para to -NH$_2$ on the benzene ring;
n is an integer equal to 0, 1 or 2;
R is alkyl, halogenated alkyl or alkoxy, each alkyl group having 1 to 4 carbon atoms and is meta or para to -NH$_2$ on the benzene ring;
p is an integer equal to 0 or 1, with the further provision that n+p is equal to 2 at most;
R$_1$ and R$_2$, which may be identical or different, are each alkyl having 1 to 4 carbon atoms or alternatively one is alkyl having 1 to 4 carbon atoms and the other is alkoxy having 1 to 4 carbon atoms; and
wherein the substituted aniline (I), excess urea (II) in a mole ratio of at least 1.1 with respect to the substituted aniline, and the secondary amine (III) are reacted simultaneously in a non-hydroxyl-containing solvent medium at a temperature of between about 130° and 250° C., with removal of ammonia (IV) as it forms.

2. A process according to claim 1 wherein n equals 2, X is Chlorine, and meta and para to -NH$_2$ on the benzene ring.

3. A process according to claim 1 wherein X is Chlorine, meta to -NH$_2$ on the benzene ring.

4. A process according to claim 1 wherein R is alkyl having 1 to 3 carbon atoms and p equals 1.

5. A process according to claim 1 wherein R is alkyl having 1 to 3 carbon atoms, para to -NH$_2$ on the benzene ring, and p equals 1.

6. A process according to claim 1 wherein R$_1$ and R$_2$ are both methyl.

7. A process according to claim 4 wherein X is chlorine, meta to -NH$_2$ on the benzene ring and R$_1$ and R$_2$ are methyl.

8. A process according to claim 1 wherein n equals O, R is isopropyl, para to -NH$_2$ on the benzene ring, and p equals 1.

9. A process according to claim 1 wherein X is chlorine, meta to -NH$_2$ on the benzene ring; R is methoxy, para to -NH$_2$ on the benzene ring and p equals 1.

10. A process according to claim 1 wherein n equals O, R is trifluoromethyl, meta to -NH$_2$ on the benzene ring, and p equals 1.

11. A process according to claim 1 wherein the temperature is between about 160° C. and 225° C.

12. A process according to claim 2 wherein the temperature is between about 160° C. and 225° C.

13. A process according to claim 4 wherein the temperature is between about 160° C. and 225° C.

14. A process according to claim 7 wherein the temperature is between about 160° C. and 225° C.

15. A process according to claim 9 wherein the temperature is between about 160° C. and 225° C.

16. A process according to claim 10 wherein the temperature is between about 160° C. and 225° C.

17. A process according to claim 1 wherein the non-hydroxy containing solvent is chlorobenzene.

18. A process according to claim 2 wherein the non-hydroxy containing solvent is chlorobenzene.

19. A process according to claim 4 wherein the non-hydroxy containing solvent is chlorobenzene.

20. A process according to claim 7 wherein the non-hydroxy containing solvent is chlorobenzene.

21. A process according to claim 9 wherein the non-hydroxy containing solvent is chlorobenzene.

22. A process according to claim 10 wherein the non-hydroxy containing solvent is chlorobenzene.

23. A process according to claim 1 wherein the mole ratio of urea to aniline is between about 1.25 and 2.

24. A process according to claim 2 wherein the mole ratio of urea to aniline is between about 1.25 and 2.

25. A process according to claim 4 wherein the mole ratio of urea to aniline is between about 1.25 and 2.

26. A process according to claim 7 wherein the mole ratio of urea to aniline is between about 1.25 and 2.

27. A process according to claim 9 wherein the mole ratio of urea to aniline is between about 1.25 and 2.

28. A process according to claim 10 wherein the mole ratio of urea to aniline is between about 1.25 and 2.

* * * * *